(12) United States Patent
Ou et al.

(10) Patent No.: US 9,907,606 B2
(45) Date of Patent: Mar. 6, 2018

(54) OPERATION TOOL OF BIPOLAR ELECTROSURGICAL INSTRUMENT

(71) Applicant: 3D GLOBAL BIOTECH INC., Taipei (TW)

(72) Inventors: Keng-Liang Ou, Kaohsiung (TW); Hsi-Jen Chiang, Taipei (TW); Chao-Chia Weng, Taipei (TW)

(73) Assignee: 3D GLOBAL BIOTECH INC., Taipei (TW)

( * ) Notice: Subject to any disclaimer, the term of this patent is extended or adjusted under 35 U.S.C. 154(b) by 126 days.

(21) Appl. No.: 14/630,304

(22) Filed: Feb. 24, 2015

(65) Prior Publication Data
US 2015/0282872 A1    Oct. 8, 2015

(30) Foreign Application Priority Data

Apr. 2, 2014    (TW) .............................. 103205639 U

(51) Int. Cl.
*A61B 18/14*    (2006.01)
*A61B 18/00*    (2006.01)

(52) U.S. Cl.
CPC ...................... *A61B 18/1445* (2013.01); *A61B 2018/00595* (2013.01)

(58) Field of Classification Search
CPC ................ A61B 18/14; A61B 18/1442; A61B 18/1445; A61B 18/1448; A61B 2018/00595
USPC .............................. 606/51–52, 169, 205–207
See application file for complete search history.

(56) References Cited

U.S. PATENT DOCUMENTS

| | | | | |
|---|---|---|---|---|
| 6,610,060 B2* | 8/2003 | Mulier | ............... | A61B 18/1445 606/49 |
| 8,262,655 B2* | 9/2012 | Ghabrial | ............ | A61B 18/1445 606/51 |
| 2001/0037109 A1* | 11/2001 | Yamauchi | .......... | A61B 18/1442 606/48 |
| 2002/0165531 A1* | 11/2002 | Goble | ................ | A61B 18/1445 606/40 |

(Continued)

FOREIGN PATENT DOCUMENTS

WO    09710756    3/1997

OTHER PUBLICATIONS

UK IPO Combined Search and Examination Report dated Jun. 30, 2015, Regarding Application No. GB1503043.0, 7 pages.

*Primary Examiner* — Michael Peffley
*Assistant Examiner* — Khadijeh Vahdat
(74) *Attorney, Agent, or Firm* — Tracy Heims; Apex Juris, pllc.

(57) ABSTRACT

A bipolar electrosurgical instrument has a handle and an operation tool. The operation tool is mounted on a front end of the handle and has multiple holes densely formed in and spread over at least one working surface of the operation tool. With the multiple holes formed on the at least one working surface of the operation tool, tissues of a surgical site can be heated uniformly and adhesion of the surgical site is minimized. Moreover, since the multiple holes are directly formed on the at least one working surface, the multiple holes do not become shallow under long-term use and no toxic gas would be released when the operation tool is heated to high temperature. Accordingly, anti-adhesion effect of the operation tool and health of medical staffs can be assured.

4 Claims, 4 Drawing Sheets

(56) References Cited

U.S. PATENT DOCUMENTS

| | | | |
|---|---|---|---|
| 2003/0055417 A1* | 3/2003 | Truckai | A61B 17/320092 606/27 |
| 2005/0101952 A1* | 5/2005 | Lands | A61B 18/1445 606/51 |
| 2005/0113828 A1* | 5/2005 | Shields | A61B 18/1442 606/51 |
| 2008/0077131 A1 | 3/2008 | Yates et al. | |
| 2010/0076432 A1* | 3/2010 | Horner | A61B 18/1442 606/52 |
| 2012/0095460 A1 | 4/2012 | Rooks | |
| 2014/0180281 A1* | 6/2014 | Rusin | A61B 18/1442 606/45 |

* cited by examiner

OPERATION TOOL OF BIPOLAR ELECTROSURGICAL INSTRUMENT

BACKGROUND OF THE INVENTION

1. Field of the Invention

The present invention relates to an electrosurgical instrument, especially to an operation tool of a bipolar electrosurgical instrument that reduces adhesions of surgical sites.

2. Description of the Prior Art(s)

Generally, surgical sites may be cut, trimmed or clipped by surgical instruments during surgical operations. An electrosurgical system is used for outputting electric current from a radio frequency power supply to the electrosurgical instruments to increase temperatures of the electrosurgical instruments. The electrosurgical instrument may be a knife, a pair of scissors, a pair of tongs, or the like. As the electrosurgical instruments are heated to high temperatures, the electrosurgical instruments can cauterize tissues to prevent blood loss when cutting, trimming or clipping the surgical sites. Thus, safety of the surgical operations can be improved.

However, when the high temperature electrosurgical instruments contact the tissues of the surgical sites, the tissues and the blood would be burned and coagulated, and adhere to the electrosurgical instruments. If the electrosurgical instruments are forced to depart from the tissues, an open wound occurs and may be enlarged, causing bleeding and elongation of surgery time. Therefore, the safety of the surgical operations is still limited.

In order to reduce adhesion of the surgical sites, an outer surface of a conventional electrosurgical instrument is coated with specific materials to form a film layer that is conductive and anti-adhesive. The film layer can heat the tissues of the surgical sites uniformly rather than heat the tissues partially, so as to prevent the adhesions of the surgical sites. Nevertheless, the specific materials would release toxic gas under high temperature, which causes harm to health of medical staffs nearby. Moreover, the film layer wears down gradually under long-term use, and effects of conduction and anti-adhesion of the film layer are reduced accordingly.

To overcome the shortcomings, the present invention provides an operation tool of a bipolar electrosurgical instrument to mitigate or obviate the aforementioned problems.

SUMMARY OF THE INVENTION

The main objective of the present invention is to provide an operation tool of a bipolar electrosurgical instrument. The bipolar electrosurgical instrument has a handle and the operation tool. The operation tool is mounted on a front end of the handle and has two holding plates and at least one working surface. Each of the at least one working surface is formed with multiple holes. The multiple holes are densely spread over the entire working surface.

With the multiple holes formed on the at least one working surface of the operation tool, tissues of a surgical site can be heated uniformly and adhesion of the surgical site is minimized. Moreover, since the multiple holes are directly formed on the at least one working surface, the multiple holes do not become shallow under long-term use and no toxic gas would be released when the operation tool is heated to high temperature. Accordingly, anti-adhesion effect of the operation tool and health of medical staffs can be assured.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
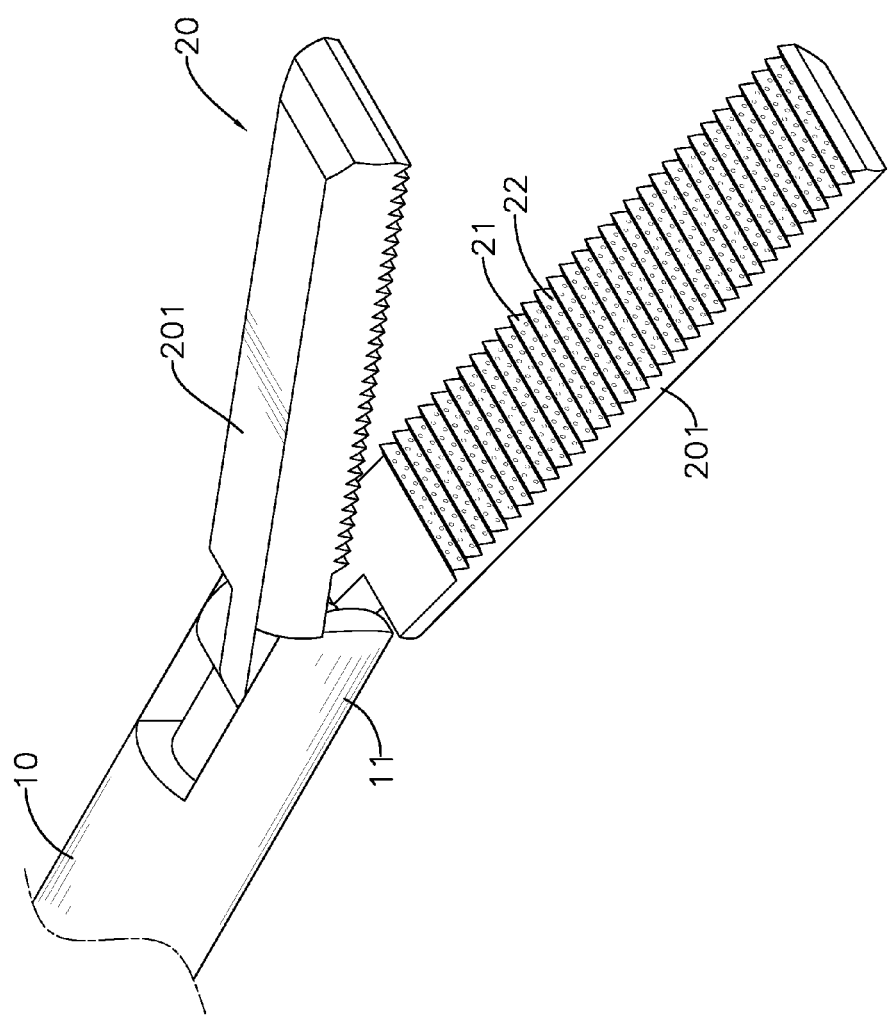
FIG. 1 is a perspective view of a first embodiment of a bipolar electrosurgical instrument in accordance with the present invention.
Figure 3:
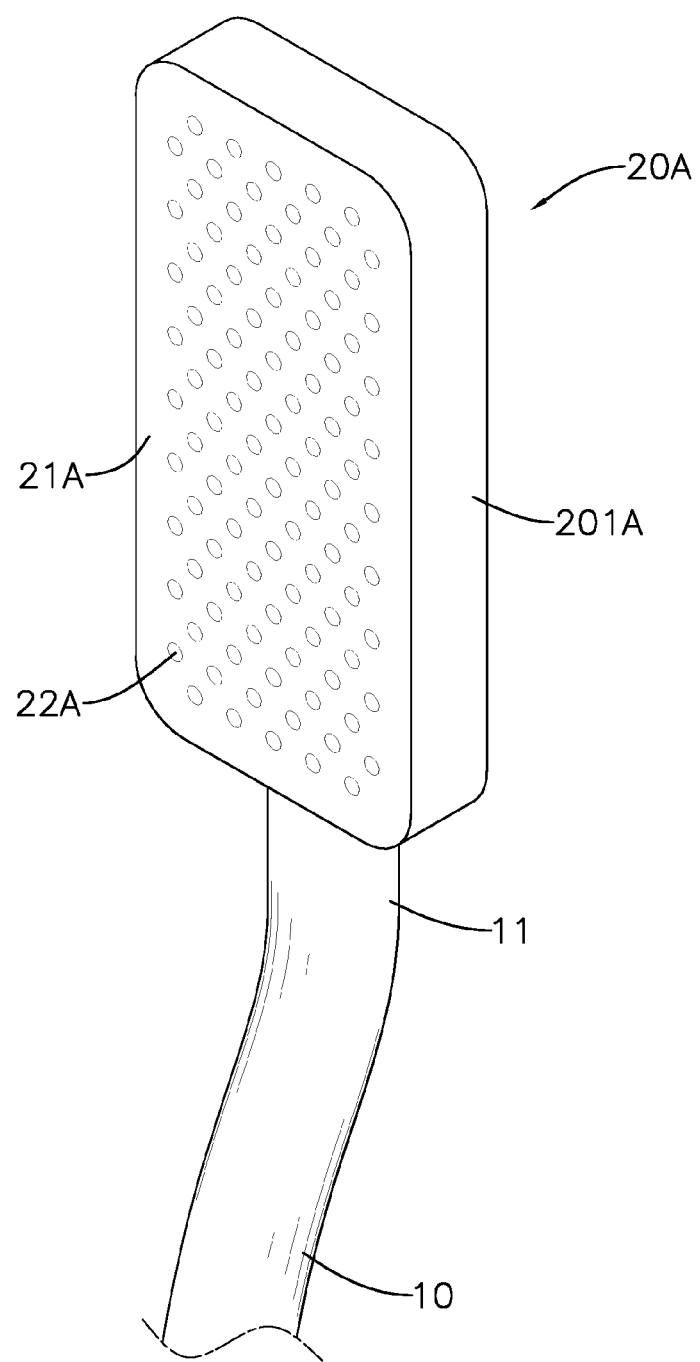
FIG. 3 is an enlarged perspective view of a second embodiment of a bipolar electrosurgical instrument in accordance with the present invention.
Figure 4:
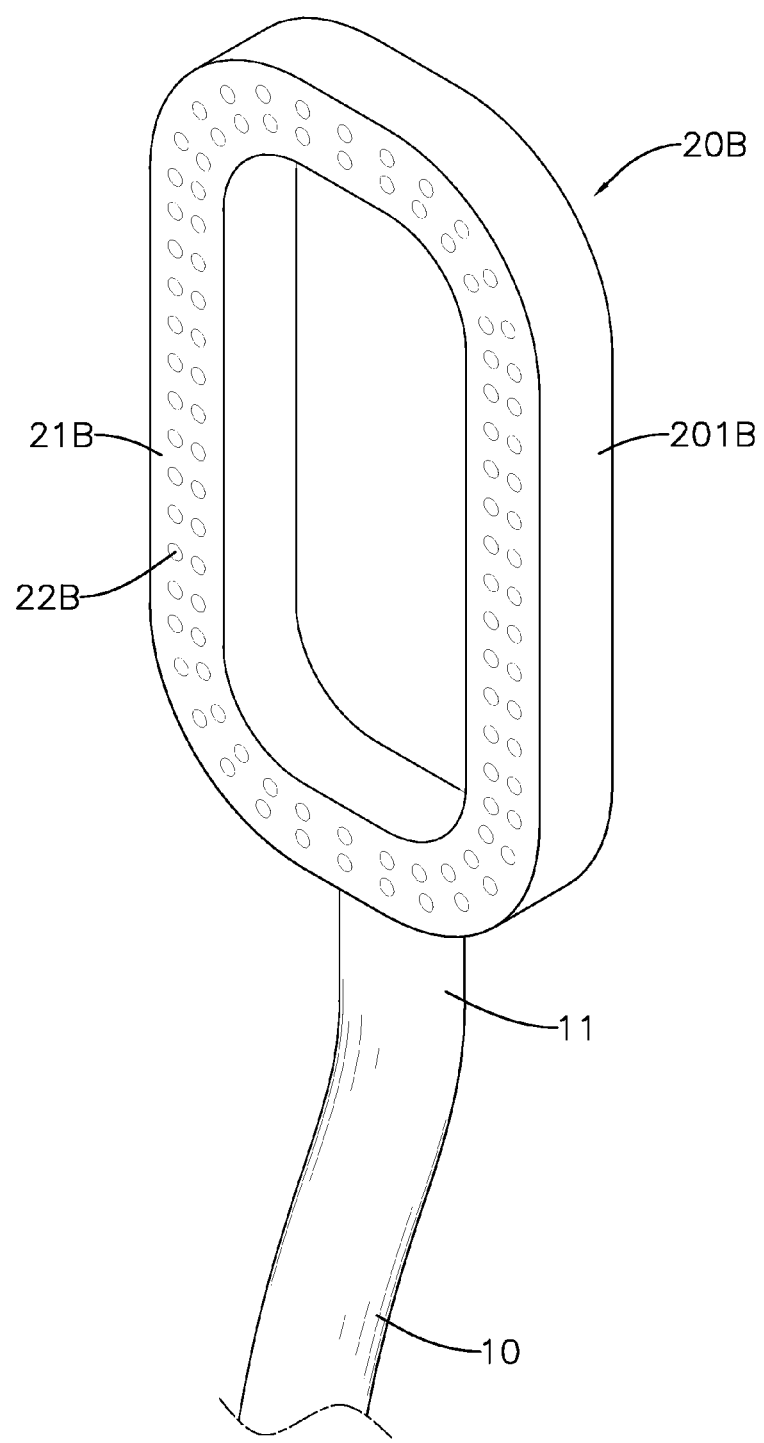
FIG. 4 is an enlarged perspective view of a third embodiment of a bipolar electrosurgical instrument in accordance with the present invention.

With reference to FIGS. 1, 3, and 4, a bipolar electrosurgical instrument comprises a handle 10 and an operation tool 20, 20A, 20B in accordance with the present invention.

The handle 10 has a rear end and a front end 11. Wires of a radio frequency power supply protrude into the handle 10 from the rear end of the handle 10 and extend to the front end 11 of the handle 10.

The operation tool 20, 20A, 20B is mounted on the front end 11 of the handle 10 and has at least one working surface 21, 21A, 21B. The at least one working surface 21, 21A, 21B is used for contacting surgical sites. Each of the at least one working surface 21, 21A, 21B is formed with multiple holes 22. The multiple holes 22 are densely spread over the entire working surface 21, 21A, 21B.

Specifically, the operation tool 20, 20A, 20B is a pair of tongs, and has two holding plates 201, 201A, 201B. The at least one working surface 21, 21A, 21B includes two working surfaces 21, 21A, 21B. The two working surfaces 21, 21A, 21B with the multiple holes 22 are respectively formed on the two holding plates 201, 201A, 201B and face each other. Alternatively, the operation tool 20, 20A, 20B may be surgical tools such as knife, a pair of scissors, or the like.

Figure 2:
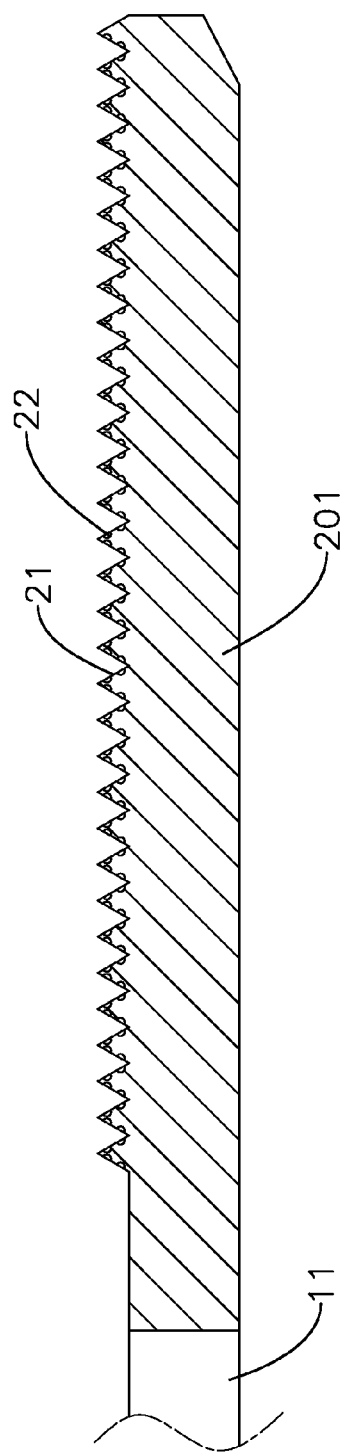
FIG. 2 is a cross-sectional side view of the bipolar electrosurgical instrument in FIG. 1.

As shown in FIGS. 1 and 2, in a first preferred embodiment, each of the two working surfaces 21 formed on the two holding plates 201 of the operation tool 20 is serrated in cross-section.

As shown in FIG. 3, in a second preferred embodiment, each of the two working surfaces 21A formed on the two holding plates 201A of the operation tool 20A is flat.

As shown FIG. 4, in a third preferred embodiment, each of the two holding plates 201B of the operation tool 20B is annular. Each of the working surfaces 21B formed on the two holding plates 201B of the operation tool 20B is flat and annular.

The bipolar electrosurgical instrument as described has the following advantages. With the multiple holes 22 formed on the at least one working surface 21, 21A, 21B of the operation tool 20, 20A, 20B, heat from the operation tool 20, 20A, 20B is accumulated in the multiple holes 22 and area of the at least one working surface 21, 21A, 21B that contacts the surgical site is greatly reduced. Thus, tissues of the surgical site can be heated uniformly, and adhesion of the surgical site is minimized. Moreover, since the multiple holes 22 are directly formed on the at least one working surface 21, 21A, 21B of the operation tool 20, 20A, 20B, the multiple holes 22 do not become shallow under long-term use. In addition, no toxic gas would be released when the operation tool 20, 20A, 20B is heated to high temperature. Accordingly, anti-adhesion effect of the operation tool 20, 20A, 20B and health of medical staffs can be assured.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An operation tool of a bipolar electrosurgical instrument, the bipolar electrosurgical instrument including a handle and a power supply, the operation tool mounted on a front end of the handle and coupled to the power supply, the operation tool comprising:

two holding plates; and two working surfaces facing each other and each one of the two working surfaces formed on each one of the two holding plates respectively, and each one of the two working surfaces adapted to allow current from the power supply to flow between the two working surfaces and a tissue of a surgical site held therebetween; and the two working surfaces formed with multiple holes, the multiple holes densely spread over an entire working area of each one of the two working surfaces so that when the tissue of the surgical site is heated via electrical current from the power supply by direct contact of the two working surfaces, the tissue between the two working surfaces is heated uniformly and adhesion of the working surfaces to the surgical site is minimized.

2. The operation tool of the bipolar electrosurgical instrument as claimed in claim 1, wherein each of the two working surfaces formed on the two holding plates of the operation tool is serrated in cross-section.

3. The operation tool of the bipolar electrosurgical instrument as claimed in claim 1, wherein each of the two working surfaces formed on the two holding plates of the operation tool is flat.

4. The operation tool of the bipolar electrosurgical instrument as claimed in claim 1, wherein each of the two holding plates of the operation tool is annular; and each of the two working surfaces formed on the two holding plates of the operation tool is flat and annular.

* * * * *